United States Patent
Zhao et al.

(10) Patent No.: US 11,633,338 B2
(45) Date of Patent: *Apr. 25, 2023

(54) MOISTURIZING HAIR CONDITIONER COMPOSITIONS CONTAINING BRASSICYL VALINATE ESYLATE

(71) Applicant: The Procter & Gamble Company, Cincinnati, OH (US)

(72) Inventors: Jean Jianqun Zhao, Cincinnati, OH (US); Heather Lynn Focht, Lebanon, OH (US); Kristi Lynn Carithers, Liberty Township, OH (US); Susanne Will, Schwalbach am Taunus (DE); Lina Aurora Witte, Monroe, OH (US); John Thomas Webber, Landen, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/398,024

(22) Filed: Aug. 10, 2021

(65) Prior Publication Data

US 2022/0047481 A1    Feb. 17, 2022

Related U.S. Application Data

(60) Provisional application No. 63/064,267, filed on Aug. 11, 2020.

(51) Int. Cl.
*A61Q 5/12* (2006.01)
*A61K 8/44* (2006.01)
*A61K 8/34* (2006.01)

(52) U.S. Cl.
CPC ............. *A61K 8/44* (2013.01); *A61K 8/342* (2013.01); *A61Q 5/12* (2013.01); *A61K 2800/30* (2013.01); *A61K 2800/524* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,321,425 A | 5/1967 | Karl-ludwig et al. |
| 3,332,880 A | 7/1967 | Adriaan et al. |
| 3,426,440 A | 2/1969 | Shen et al. |
| 3,463,308 A | 8/1969 | Deneke |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,051,081 A | 9/1977 | Jabs et al. |
| 4,089,945 A | 5/1978 | Brinkman et al. |
| 4,149,551 A | 4/1979 | Benjamin et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |
| 4,565,647 A | 1/1986 | Llenado |
| D286,450 S | 10/1986 | Tovey |
| 4,663,158 A | 5/1987 | Wolfram et al. |
| 4,710,374 A | 12/1987 | Grollier et al. |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,104,646 A | 4/1992 | Bolich, Jr. |
| 5,106,609 A | 4/1992 | Bolich, Jr. |
| 5,166,276 A | 11/1992 | Hayama et al. |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

PCT Search Report and Written Opinion for PCT/US2021/071145 dated Dec. 6, 2021, 15 pages.

(Continued)

*Primary Examiner* — Jyothsna A Venkat
(74) *Attorney, Agent, or Firm* — Kathleen Y. Carter

(57) ABSTRACT

A hair conditioner composition comprising: a. an aqueous carrier; b. from about 1 wt % to about 12 wt % of BVE; and c. from about 1 wt % to about 12 wt % of at least two fatty alcohols.

7 Claims, 3 Drawing Sheets

(56) References Cited

U.S. PATENT DOCUMENTS

| | | |
|---|---|---|
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,476,597 A | 12/1995 | Sakata et al. |
| 5,501,238 A | 3/1996 | Borstel et al. |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| 5,885,561 A | 3/1999 | Flemming et al. |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. et al. |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D442,739 S | 5/2001 | Friesenhahn |
| 6,225,252 B1 | 5/2001 | Ernst et al. |
| D443,389 S | 6/2001 | Friesenhahn |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D484,749 S | 1/2004 | Garraway |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| 8,828,370 B2 | 9/2014 | Yang et al. |
| D739,227 S | 9/2015 | Mitchell et al. |
| D740,928 S | 10/2015 | Bruining et al. |
| 9,198,838 B2 | 12/2015 | Glenn, Jr. |
| D769,522 S | 10/2016 | Venet |
| 9,539,444 B2 | 1/2017 | Kinoshita et al. |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| 10,294,586 B2 | 5/2019 | Sivik et al. |
| D851,344 S | 6/2019 | Carlson et al. |
| D857,156 S | 8/2019 | Hani |
| 10,413,496 B2 | 9/2019 | Pistorio et al. |
| D862,020 S | 10/2019 | Gorrell et al. |
| D866,893 S | 11/2019 | Hunt et al. |
| D867,717 S | 11/2019 | Chavez |
| D868,953 S | 12/2019 | Mckendree |
| 10,569,286 B2 | 2/2020 | Anderson et al. |
| 10,694,917 B2 | 6/2020 | Dreher et al. |
| D910,434 S | 2/2021 | Tan et al. |
| D910,457 S | 2/2021 | Lee |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0082129 A1 | 5/2003 | Buckingham et al. |
| 2003/0099691 A1 | 5/2003 | Lydzinski et al. |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |

(56) References Cited

U.S. PATENT DOCUMENTS

| | | |
|---|---|---|
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0024256 A1 | 2/2006 | Wells et al. |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona et al. |
| 2006/0274263 A1 | 12/2006 | Yacktman et al. |
| 2006/0286060 A1 | 12/2006 | Yang et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0166272 A1 | 7/2007 | Kaharu |
| 2007/0225388 A1 | 9/2007 | Cooper et al. |
| 2007/0237736 A1 | 10/2007 | Burgo et al. |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150858 A1 | 6/2010 | Runglertkriangkrai |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0274641 A1 | 11/2011 | Burgo |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105942 A1 | 4/2014 | Pistorio et al. |
| 2014/0329428 A1 | 11/2014 | Glenn, Jr. |
| 2015/0017218 A1 | 1/2015 | Pettigrew et al. |
| 2015/0250701 A1 | 9/2015 | Hamersky et al. |
| 2015/0290109 A1 | 10/2015 | Simonnet et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0158134 A1 | 6/2016 | Disalvo |
| 2016/0243007 A1 | 8/2016 | Constantine et al. |
| 2016/0250109 A1 | 9/2016 | Dreher et al. |
| 2016/0361242 A1 | 12/2016 | Durtschi et al. |
| 2016/0367104 A1 | 12/2016 | Dreher et al. |
| 2017/0056300 A1 | 3/2017 | Constantine et al. |
| 2017/0056301 A1 | 3/2017 | Constantine et al. |
| 2017/0121641 A1 | 5/2017 | Smith |
| 2017/0335080 A1 | 11/2017 | Mao et al. |
| 2018/0028435 A1 | 2/2018 | Punsch et al. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2018/0360702 A1 | 12/2018 | Demarcq et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0161780 A1 | 6/2021 | Zhao et al. |
| 2021/0161784 A1 | 6/2021 | Zhao et al. |

FOREIGN PATENT DOCUMENTS

| | | |
|---|---|---|
| CN | 1268558 A | 10/2000 |
| CN | 1357613 A | 7/2002 |
| CN | 1530431 A | 9/2004 |
| CN | 1583991 A | 2/2005 |
| CN | 106726634 A | 5/2017 |
| CN | 106728634 A | 5/2017 |
| DE | 19607851 A1 | 9/1997 |
| DE | 10331767 A1 | 2/2005 |
| DE | 102010026747 A1 | 1/2012 |
| DE | DM100932 | 4/2018 |
| DE | DM100938 | 4/2018 |
| DE | DM101063 | 5/2018 |
| DE | DM101100 | 5/2018 |
| DE | DM101101 | 5/2018 |
| EP | 609808 A1 | 8/1994 |
| EP | 0858828 A1 | 8/1998 |
| EP | 1206933 A1 | 5/2002 |
| EP | 1217987 B1 | 12/2004 |
| EP | 1160311 B1 | 3/2006 |
| EP | 2085434 A1 | 8/2009 |
| EP | 3622946 A1 | 3/2020 |
| FR | 2886845 A1 | 12/2006 |
| FR | 2967054 A1 | 5/2012 |
| FR | 2992217 A1 | 12/2013 |
| GB | 2235204 A | 2/1991 |
| JP | 58021608 S | 2/1983 |
| JP | S58216109 A | 12/1983 |
| JP | S6272609 A | 4/1987 |
| JP | S6272610 A | 4/1987 |
| JP | S6281432 A | 4/1987 |
| JP | H01172319 A | 7/1989 |
| JP | H01313418 A | 12/1989 |
| JP | H0275650 A | 3/1990 |
| JP | H05344873 A | 12/1993 |

(56) References Cited

FOREIGN PATENT DOCUMENTS

| | | | |
|---|---|---|---|
| JP | H0617083 A | 1/1994 |
| JP | 0753349 A | 2/1995 |
| JP | H0789852 A | 4/1995 |
| JP | H08325133 A | 12/1996 |
| JP | H10251371 A | 9/1998 |
| JP | 2000053998 A | 2/2000 |
| JP | 2003073700 A | 3/2003 |
| JP | 2003082397 A | 3/2003 |
| JP | 2003113032 A | 4/2003 |
| JP | 2004256799 A | 9/2004 |
| JP | 2004345983 A | 12/2004 |
| JP | 2005171063 A | 6/2005 |
| JP | 2007091954 A | 4/2007 |
| JP | 2007197540 A | 8/2007 |
| KR | 20020003442 A | 1/2002 |
| KR | 20180012903 A | 2/2018 |
| KR | 20200058938 A | 5/2020 |
| WO | 8301943 A1 | 6/1983 |
| WO | 9514495 A1 | 6/1995 |
| WO | 0112134 A2 | 2/2001 |
| WO | 0119948 A1 | 3/2001 |
| WO | 0125393 A1 | 4/2001 |
| WO | 200125322 A1 | 4/2001 |
| WO | 2001024770 A1 | 4/2001 |
| WO | 2001054667 A1 | 8/2001 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2007033598 A1 | 3/2007 |
| WO | 2007093558 A1 | 8/2007 |
| WO | 2009019571 A2 | 2/2009 |
| WO | 2009095891 A1 | 8/2009 |
| WO | 2010077627 A2 | 7/2010 |
| WO | 2010085569 A1 | 7/2010 |
| WO | 2011113501 A1 | 9/2011 |
| WO | 2012120199 A1 | 9/2012 |
| WO | 2012172207 A2 | 12/2012 |
| WO | 2013150044 A2 | 10/2013 |
| WO | 2017096479 A1 | 6/2017 |
| WO | 2018023180 A1 | 2/2018 |
| WO | 2018098542 A1 | 6/2018 |
| WO | 2019001940 A1 | 1/2019 |
| WO | 2019014868 A1 | 1/2019 |
| WO | 2019090098 A1 | 5/2019 |

OTHER PUBLICATIONS

All Office Actions; U.S. Appl. No. 17/398,025, filed Aug. 10, 2021.
All Office Actions; U.S. Appl. No. 17/398,020, filed Aug. 10, 2021.
All Office Actions; U.S. Appl. No. 17/108,081, filed Dec. 1, 2020.
All Office Actions; U.S. Appl. No. 17/108,090, filed Dec. 1, 2020.
All Office Actions; U.S. Appl. No. 17/209,292, filed Mar. 23, 2021.
Anonymous "P8136 Poly(vinyl alcohol)" Internet article, [Online] XP002538935, Retrieved from the Internet: URL: hllp/20 NWW. sigmaaldrich.com/catalog/ProductDetail.do?D7=0%N25-SEARCH_ CONCAT PNOIBRAND KEY%N4=P8136%7SCIAL% N25=0%QS=ON%F=SPEC retrieved on Jul. 28, 2009, year 2009, 1 pg.
Briscoe et al. "The effects of hydrogen bonding upon the viscosity of aqueous poly( vinyl alcohol) solutions," from Polymer, 41 (2000), pp. 3851-3860.
Database GNPD [Online]MINTEL; Sep. 19, 2019 (Sep. 19, 2019), anonymous: "Conditioner", XP055779509, 3 pgs.
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Encyclopedia of Polymer Science and Engineering, vol. 15, 2nd ed., pp. 204-308 Silicones, year 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet : http://candlebox.com/product/%EC%9C%A1%EA%B0%81-4%EA%B5%AC-%EB%B9%84%EB%88%84%EB%AA%B0 %EB%93%9C/2206/?page_4=3#none, dated Sep. 10, 2019, 16 pgs.
Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014] (Copy not provided).
Michelle Villett, Why You Need a Sulfate-Free Shampoo, The Skincare Edit, updated date: Jan. 25, 2019, Original publication date: Feb. 22, 2016 (Year: 2016), 7 pages.
Miller Robert et al. "Bio-basedpropanediol boosts preservative efficacy",Personal Care, Apr. 1, 2012 (Apr. 1, 2012), pp. 1-4,XP055773579.
N Konate et al: "Sustainably Sourced Pentylene Glycol—a Green All-Rounder",SOFW Journal: Seifen, Ole, Fette, Wachse,vol. 10, No. 142, Oct. 1, 2016 (Oct. 1, 2016), pp. 44-51,XP055747004.
Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.
Retrieved from: https ://www.craftcuts.com/hexagon-craft-shape. html Hexagon wood cutouts, www.craftcuts.com, 1 page, reviewed as early as May 2018 (Year: 2018), 16 pgs.
U.S. Appl. No. 17/398,020, filed Aug. 10, 2021, to Jean Jianqun Zhao et. al.
U.S. Appl. No. 17/398,025, filed Aug. 10, 2021, to Jean Jianqun Zhao et. al.
U.S. Appl. No. 17/209,292, filed Mar. 23, 2021, to Jennifer Mary Marsh et. al.
Vaughan, C.D. "Solubility, Effects in Product, Package, Penetration and Preservation", Cosmetics and Toiletries, vol. 103, Oct. 1988, 24 pgs.
Vesterby, A.: "Star Volume in Bone Research: A Histomorphometric Analysis Of Trabecular Bone Structure Using Vertical Sections", Anal Rec: Feb. 1993, 232(2), pp. 325-334.
Zhang et al. "Study on Morphology of Electrospun Poly( vinyl alcohol) Mats," European Polymer Journal 41 (2005), pp. 423-432.
Third Party Observation for PCT/US2021/071145 dated Dec. 9, 2022, 2 pages.

Fig. 2A

| | |
|---|---|
| Natural Credentials | |
| Brassicyl Valinate Esylate (AminoSensyl™ from Inolex) | |
| Behenamidopropyl Dimethylamine (BAPDMA) + L-Glutamic Acid | |
| Stearamidopropyl Dimethylamine (SAPDMA) + L-Glutamic Acid | |
| Behentrimonium Chloride (BTMAC) | |
| Behentrimonium Methosulfate (BTMS) | |

| EWG Verified | Whole Food List | Yuka Risk Free | COSMOS Natural | ECOCERT Natural |
|---|---|---|---|---|
| Allowed | Allowed | Green | Certified | Certified |
| Allowed | Allowed | Green | Not Certified | Not Certified |
| Allowed | Un-acceptable | Green | Not Certified | Not Certified |
| Un-acceptable | Allowed | Warning | Not Certified | Not Certified |
| Un-acceptable | Allowed | Warning | Not Certified | Not Certified |

MOISTURIZING HAIR CONDITIONER COMPOSITIONS CONTAINING BRASSICYL VALINATE ESYLATE

FIELD OF THE INVENTION

The present invention relates to hair conditioner compositions, more particularly to hair conditioner compositions comprising brassicyl valinate esylate bio-based cationic amino lipid.

BACKGROUND OF THE INVENTION

A variety of approaches have been developed to condition the hair. These approaches range from post-shampoo application of hair conditioners such as leave-on and rinse-off products, to hair conditioning shampoos which attempt to both clean and condition the hair from a single product.

Although some consumers prefer the ease and convenience of a shampoo which includes conditioners, a substantial proportion of consumers prefer the more conventional conditioner formulations which are applied to the hair as a separate step from shampooing, usually subsequent to shampooing. Conditioning formulations can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or amount of hair.

There is growing demand from the public for a reduction or elimination of certain ingredients, including certain surfactants and preservatives, in hair care products. Some consumers want the ingredients in their hair care products to meet natural credentialing standards, such as to be EWG VERIFIED™, to be free of any of the ingredients that Whole Foods® lists as unacceptable for body care, and to be categorized as "risk-free" (green dot) by the Yuka® Application. Hair care products may also meet the COSMOS-standard (Jan. 1, 2019). The COSMOS-standard's ultimate objective is to address the major issues essential to the environment and welfare of humans on the planet.

However, modifying the materials used in hair care products can negatively impact the product. For example, in conditioners, modifying the cationic surfactant can decrease conditioning performance and modifying the preservative system can have a negative impact on microbiological safety requirements.

Therefore, there is a need for a conditioner composition that meets COSMOS and other natural credentialing standards, while still delivering the performance consumers expect and desire.

SUMMARY OF THE INVENTION

A hair conditioner composition comprising:
a. an aqueous carrier;
b. from about 1 wt % to about 12 wt % of BVE; and
c. from about 1 wt % to about 12 wt % of at least two fatty alcohols;
wherein the first fatty alcohol has an alkyl chain average equal to or lower than C16 and the second fatty alcohol has an alkyl chain average equal to or higher than C18; and wherein from 0.2 wt % to 8 wt % of the composition is a fatty alcohol having an alkyl chain average of C22;
wherein the molar ratio of the first fatty alcohol to the second fatty alcohol is from about 25:75 to 90:10;
wherein the molar ratio of BVE to total fatty alcohol is from about 20:80 to about 45:55;
wherein the composition comprises a uniform $L\beta$ gel network;
wherein the composition comprises d-spacing of from about 15 nm to about 40 nm, as measured according to the d-spacing ($L\beta$-basal spacing) of Lamella Gel Network Test Method; and
wherein the composition has a shear stress from about 70 Pa to 800 Pa @ 950 l/s.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIGS. 2A and 2B show the chemical structure comparison of cationic surfactants and their natural credentials.

DETAILED DESCRIPTION OF THE INVENTION

While the specification concludes with claims particularly pointing out and distinctly claiming the invention, it is believed that the present invention will be better understood from the following description.

Hair conditioners are used to improve the feel, appearance, and manageability of the hair. Hair conditioning compositions generally include cationic surfactant(s), high melting point fatty compound(s) having a melting point of greater than 25° C. and in some examples from 40 to 85° C., and an aqueous carrier. The ingredients in current hair conditioners, including the cationic surfactant and preservative system, are generally recognized as safe and effective.

However, there is growing demand from the public for a conditioner product and/or a preservative system that meets at least one, two, three, or all four of the following standards:
- EWG VERIFIED™ (according to the criteria, as of Nov. 25, 2019), which includes meeting the Environmental Working Group's (EWG) criteria including avoiding EWG's ingredients of concern, having fully transparent labeling, and using good manufacturing practices, in addition to other criteria described in EWG's Licensing Criteria: Personal Care Products (2019).
- Does not contain any of ingredients that Whole Foods® lists as unacceptable in its Premium Body Care Unacceptable Ingredients (July 2018)
- Categorized as "risk-free" (green dot) by the Yuka® Application (March 2019)
- COSMOS-standards (2019)

However, replacing traditional cationic surfactants, such as behentrimonium chloride (BTMAC), which is restricted by the Environmental Working Group (EWG) for use in the cosmetic products as of Nov. 25, 2019 and/or stearamidopropyl dimethylamine (SAPDMA), which is an unacceptable ingredient listed on the Whole Foods® Premium Body Care Unacceptable Ingredients (July 2018), and preservatives with ingredients that meet the standards, listed above, while maintaining product performance and antimicrobial effectiveness can be challenging. Most of the commonly used cationic surfactants in hair conditioners, such as quaternized ammonium salts consist of behentrimonium chloride (BTMAC) and behentrimonium methosulfate (BTMS), and tertiary amidoamines consist of stearamidopropyl dimethylamine (SAPDMA), brassicamidopropyl dimethylamine (BrassAPDMA) and behenamidopropyl dimethylamine (BAPDMA), are not COSMOS Natural or Ecocert Natural certified, as shown in FIG. 2.

Figure 1:
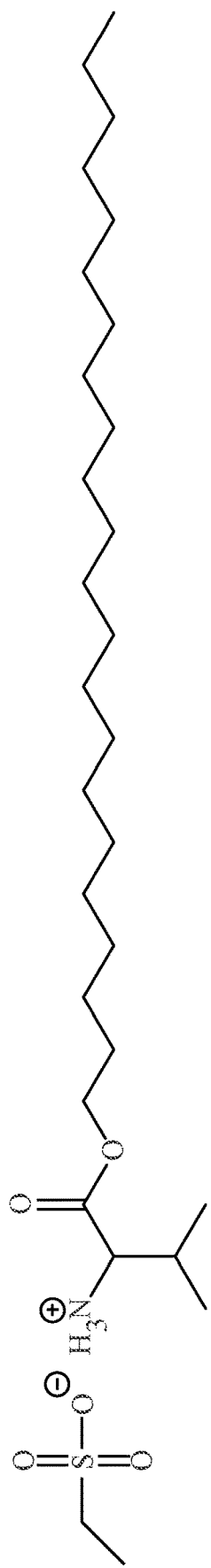
FIG. 1 shows the chemical structure for Brassicyl Valinate Esylate (BVE).

Brassicyl valinate esylate (BVE), with the structure shown in FIG. 1, was identified as a cationic surfactant that can meet the standards, above. It is certified by COSMOS Natural or Ecocert Natural. Further details regarding BVE may be found in U.S. Pat. Nos. 8,287,844 and 8,105,569, the substance of both which are incorporated herein by reference.

Figure 2:
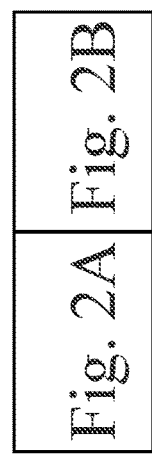
FIG. 2 shows how the charts of FIGS. 2A and 2B should be viewed.

However, it can be hard to formulate effective conditioner compositions that contain BVE because BVE is much more hydrophobic than the traditional cationic surfactants, as shown in the structure comparison chart in FIG. 2. The BVE has a smaller hydrophilic head group (as shown by the shading) and steric hindrance of the isopropyl alkyl chain connected to the head group that prevents the surfactant and fatty alcohol(s) packing during the melt stage to form a good gel network. The gel network formed is more hydrophobic than the conventional ones, which leads to a conditioner with poor wet conditioning performance, such as not spreading on hair easily, not detangling wet hair well, not rinsing-off quickly, and not feeling clean after use.

This is a common drawback for using natural conditioners on the markets today. Most of the natural conditioners do not have a good gel network, especially comprising COSMOS listed ingredients, as shown in table below.

Table 1 shows Herbal Essences® Honey & Vitamin B conditioner, which contains BTMAC, and Herbal Essences® Refresh Blue Ginger conditioner, which contains SAPDMA. Both have good Lβ gel networks with well-defined d-spacing.

Kerastase® Aura Botanica is a marketed natural conditioner, which contains a cationic surfactant brassicamidopropyl dimethylamine (BrassAPDMA) which is not COSMOS certified. It has a large Lβ d-spacing of 43, and additional unincorporated material as detected by x-ray, meaning it is not a good gel network.

Weleda® Oat Replenishing conditioner, which does not contain a cationic surfactant, and Avalon Organic® conditioner, which contains COSMOS natural certified cationic surfactant Brassicyl Isoleucinate Esylate (BIE), Lβ gel networks were not detected by x-ray.

TABLE 1

Gel Network and Natural Credential of Current Products vs. Examples 1-21

|  | Herbal Essences® Honey & Vitamin B Conditioner | Herbal Essences® Refresh Blue Ginger | Kerastase® Aura Botanica | Weleda® Oat Replenishing | Avalon Organic® Tea Tree | Invented Examples 1-21 |
|---|---|---|---|---|---|---|
| Primary Cationic Surfactant | BTMAC | SAPDMA | BrassAPDMA |  | BIE | BYE |
| Is Primary Cationic Surfactant COSMOS Natural Certified? | No | No | No | N/A | Yes | Yes |
| Lβ gel network | Well formed | Well formed | additional unincorporated material detected | Not detected | Not detected | Well formed |
| d-spacing (nm) | 24.2 | 34 | 43 | n/d | n/d | 15-40 |

It was surprisingly found that Lβ gel network is well formed in the inventive conditioner compositions (see Table 7 to Table 11, below). The presence of Lβ gel network has been confirmed by wide-angle x-ray scattering (WAXS). The d-spacing (Lβ-basal spacing) of the lamella gel network for the inventive conditioner compositions is from about 15 nm to about 40 nm, as measured by small-angle x-ray scattering (SAXS). The conditioners provide good wet conditioning, clean feel, volume, and consumer preferred rheology (sheer stress).

While not willing to be bound by theory, it is believed that the molar ratio of BVE to fatty alcohol(s) and the molar ratio of short chain (C16 or lower) fatty alcohol to long chain (C18 or higher) fatty alcohol, can result in a conditioner composition gel network and good d-spacing from 15 to 40 nm, which provides good conditioning performance including a good slippery feel and wet detangling.

Furthermore, the conditioners in Ex. 1 to Ex. 21 (Table 7 to Table 11) had a uniform gel network and are stable, meaning no phase separation. The Lβ gel network's thermal behaviors have been measured by Differential Scanning calorimetry Test Method.

Also, conditioner compositions that provide good wet conditioning may weigh down hair causing a loss of dry hair volume and/or may cause the hair to feel dirty and/or oily quickly, which can result in consumers washing their hair more frequently. It was found that the hair conditioner compositions of Ex. 1 to Ex. 21 may not only provide good hair conditioning but may also give good hair volume and/or provide a long-lasting clean feel, allowing ease of styling.

Furthermore, Tables 7 to 11 below include examples that have a sodium benzoate or potassium sorbate as a preservative, which meets the standards for controlling microbial growth. However, the present inventors discovered that if the conditioner composition had a smooth and creamy consistency, then the level of sodium benzoate was too low to effectively inhibit the growth of microbes. When the level of sodium benzoate or potassium sorbate was increased, the conditioner composition was too thin to easily apply with a user's hands, which can significantly impact product performance and the usage experience. As shown in Table 7 and described in the accompanying text, a preservative system with sodium benzoate or potassium sorbate and a glycol, such as caprylyl glycol, or glyceryl esters, such as glyceryl caprylate/caprate and glyceryl caprylate (and) glyceryl undecylenate, can be more effective if the proper levels of each ingredient are added.

It was found that a preservative system that contains sodium benzoate or potassium sorbate and a second preservative composition selected from the group consisting of glycols, glyceryl esters, and combinations thereof contains all of the ingredients that have a EWG rating score of equal to or less than 3, can be EWG VERIFIED™, may not contain any of the ingredients that Whole Foods® Market lists as unacceptable, can be categorized as "risk-free" by the Yuka® Application, and can also meet the COSMOS-standard (Jan. 1, 2019), while maintaining antimicrobial effectiveness providing good conditioning performance.

The second preservative composition can contain a glycol and/or a glyceryl ester. Glycols and glyceryl esters both have two —OH groups on the molecule. Non-limiting examples of glycols can include butylene glycol, pentylene glycol, hexylene glycol, 1,2-hexanediol, caprylyl glycol, decylene glycol (1,2-decanediol) and mixtures thereof. In one example, the glycol can be carpylyl glycol. Non-limiting examples of glycerol esters can include glyceryl caprylate, glyceryl caprate, glyceryl undecylenate and mixtures thereof.

The conditioner compositions containing this preservative system can have a uniform, smooth, creamy appearance and have an effective preservative system where the level of microbes (both bacteria and fungi) is undetectable (>99.99% reduction) as determined by the Bacterial and Fungal Microbial Susceptibility Test Methods, as described herein.

The conditioner composition and/or preservative system can be free of or substantially free of certain preservatives, in particular preservatives that do not meet one or more of the requirements, such as ethylenediaminetetraacetic acid (EDTA) and salts thereof, isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, and/or parabens.

In addition to meeting the standards for a cationic surfactant and preservative system, some consumers prefer a conditioner composition that is free of or substantially free of the following: silicone, propellants, phthalates, parabens, isothiazolinones (e.g. Kathon™), phenoxyethanols, dyes, sulfates, and/or formaldehyde donors. The conditioner composition can also be vegan.

The conditioner composition can be free of or substantially free of quaternized ammonium salt such as behentrimonium chloride, behentrimonium methosulfate, cetrimonium chloride, and free of amidoamine such as stearamidopropyl dimethylamine, brassicamidopropyl dimethylamine, and behenamidopropyl dimethylamine.

The conditioner composition can contain at least about 1.0 wt % BVE, alternatively at least about 1.1 wt % BVE, alternatively at least about 1.2 wt % BVE. The conditioner composition can contain from about 1.0 wt % to about 12 wt % BVE, alternatively from about 1.2 wt % to about 10 wt %, alternatively from about 1.5 wt % to about 10 wt % BVE, alternatively from about 1.5 wt % to about 8 wt %.

The conditioner composition can contain from about 1 wt % to about 12 wt % of at least two fatty alcohols. The total fatty alcohol amount may be from about 1 wt % to about 12 wt % of the composition, alternatively from about 1.2 wt % to about 11 wt % of the composition, or 1.5 wt % to about 10 wt % of the composition. The first fatty alcohol may have an alkyl chain average of C16 or lower. The second fatty alcohol may have an alkyl chain average of C18 or higher. The first fatty alcohol may have an alkyl chain average of C14 to C16. The second fatty alcohol may have an alkyl chain average from C18 to C22. The molar ratio of the first fatty alcohol to the second fatty alcohol may be from about 25:75 to about 95:5, alternatively from about 25:75 to about 90:10, alternatively from about 30:70 to about 90:10, alternatively from about 35:65 to about 90:10.

The fatty alcohol may be selected from the group consisting of lauryl alcohol (C12), tridecyl alcohol (C13), myristyl alcohol (C14), pentadecyl alcohol (C15), cetyl alcohol (C16), isocetyl alcohol (C16), palmitoleyl alcohol (C16), heptadecyl alcohol (C17), stearyl alcohol (C18), isostearyl alcohol (C18), oleyl alcohol (C18), nonadecyl alcohol (C19), arachidyl alcohol (C20), heneicosyl alcohol (C21), behenyl alcohol (C22) erucyl alcohol (C22), lignoceryl alcohol (C24), ceryl alcohol (C26), brassica alcohol (C18-C22), cetostearyl alcohol (C16-C18), cetearyl alcohol (C16-C18), cetylstearyl alcohol (C16-C18) and combinations thereof.

The conditioner composition can have a molar ratio of BVE to total fatty alcohol from about 20:80 to about 45:55, alternatively from about 20:80 to 35:65, or from about 20:80 to 40:60.

The conditioner compositions may contain a gel network comprising BVE and fatty alcohol(s). The composition may have a total gel network (GN) content, which is the sum of BVE and fatty alcohol(s) (FAOH), of from about 0.016 molar to about 0.06 molar, alternatively from about 0.016 molar, to about 0.055 molar, or alternatively from about 0.017 to about 0.05 molar.

The conditioner composition can have d-spacing of from about 15 nm to about 40 nm, alternatively from 15 to 35, and alternatively from 15 to 32. The d-spacing is determined by the d-spacing (Lβ-basal spacing) of Lamella Gel Network Test Method, described herein.

The conditioner composition can contain from about 0.1 wt % to about 2.5 wt % preservative system, alternatively from about 0.15 wt % to about 1.5 wt % preservative system, alternatively from about 0.2 wt % to about 1.4 wt % preservative system, alternatively from 0.2 wt % to about 1.8 wt % preservative system, and alternatively from about 0.3 wt % to about 1.6 wt % preservative system.

The first preservative ingredient may be selected from the group consisting of sodium benzoate, potassium sorbate, sodium salicylate, sodium chloride, sodium carbonate, sodium borate, sodium acetate, sodium citrate, potassium benzoate, potassium acetate, calcium gluconate, calcium chloride, and combinations thereof.

The conditioner composition can contain from about 0.05 wt % to about 0.8 wt % of the first preservative.

The conditioner composition can contain from about 0.05 wt % to about 0.8 wt % sodium benzoate, alternatively 0.1 wt % to about 0.5 wt % sodium benzoate, alternatively from about 0.2 wt % to about 0.4 wt % sodium benzoate or potassium sorbate. The conditioner composition can contain sodium benzoate or potassium sorbate and can contain less than 2% sodium benzoate or potassium sorbate, alternatively less than 1.5% sodium benzoate or potassium sorbate, alternatively less than 1% sodium benzoate or potassium sorbate, alternatively less than 0.8% sodium benzoate or potassium sorbate, alternatively less than 0.6 wt % sodium benzoate or potassium sorbate, and alternatively less than 0.5% sodium benzoate or potassium sorbate.

The conditioner composition can contain from about 0.2 wt % to about 2.5 wt % of a second preservative composition, alternatively from about 0.3 wt % to about 2 wt %, alternatively from about 0.4 wt % to about 1.5 wt %, alternatively from about 0.4 wt % to about 1.3 wt %, alternatively from about 0.3 wt % to about 1.2 wt %, alternatively from about 0.3 wt % to about 1.1 wt %, and alternatively from about 0.35 wt % to about 1.1 wt %. If the conditioner composition contains too much glycol and/or glyceryl esters the gel network structure may be destroyed, and the conditioner will not have consumer acceptable rheology and/or performance.

The second preservative ingredient may be a glyceryl ester selected from the group consisting of glyceryl caprylate, glyceryl caprate, glyceryl undecylenate and mixtures thereof, or a glycol selected from the group consisting of butylene glycol, pentylene glycol, hexylene glycol, 1,2-hexanediol, caprylyl glycol, decylene glycol, and mixtures thereof, and combinations thereof. The conditioner composition can have a shear stress from about 70 Pa to about 800 Pa, alternatively from about 75 Pa to about 700 Pa, alternatively from 78 Pa to 650 Pa. The shear stress can be determined using the Shear Stress Test Method, described hereafter.

The conditioner composition can have a pH of less than 5.5. Alternatively, the conditioner composition can have a pH from about 2.5 to about 5.5, alternatively from about 3.0 to about 5.0. The pH can be determined using the pH Test Method, described hereafter.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, the terms "include," "includes," and "including," are meant to be non-limiting and are understood to mean "comprise," "comprises," and "comprising," respectively.

As used herein, the term "free of" means that 0% of an ingredient was intentionally added to the conditioner composition, or the conditioner composition comprises 0% of an ingredient by total weight of the composition, thus no detectable amount of the stated ingredient.

The term "substantially free of" as used herein means less than 0.5%, less than 0.3%, less than 0.1%, less than 0.05%, less than 0.01%, or less than an immaterial amount of a stated ingredient by total weight of the composition.

As used herein, "mixtures" is meant to include a simple combination of materials and any compounds that may result from their combination.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cationic Surfactant

The compositions of the present invention can comprise a cationic surfactant. The cationic surfactant can be included in the composition at a level of from about 0.1 wt %, alternatively from about 0.5 wt %, alternatively from about 0.8 wt %, alternatively from about 1.0 wt %, alternatively from about 1.0 wt %, and to about 20 wt %, alternatively to about 18 wt %, alternatively to about 15 wt %, alternatively to about 12 wt % by weight of the composition, in view of providing the benefits of the present invention.

The surfactant can be water-insoluble. In the present invention, "water-insoluble surfactants" means that the surfactants have a solubility in water at 25° C. of alternatively below 0.5 g/100 g (excluding 0.5 g/100 g) water, alternatively 0.3 g/100 g water or less.

Cationic surfactant can be one cationic surfactant or a mixture of two or more cationic surfactants. Alternatively, the cationic surfactant is selected from: a mono-long alkyl amine; a di-long alkyl quaternized ammonium salt; a mono-long alkyl cationic neutralized amino acid esters; a combination of a mono-long alkyl amine and a di-long alkyl quaternized ammonium salt; and a combination of a mono-long alkyl amine and a mono-long alkyl cationic neutralized amino acid esters.

In some examples, the conditioner composition can be substantially free of or free of cationic surfactants that have a quaternized ammonium salt.

Mono-Long Alkyl Amine

Mono-long alkyl amine can include those having one long alkyl chain of alternatively from 19 to 30 carbon atoms, alternatively from 19 to 24 carbon atoms, alternatively from 20 to 24 carbon atoms, alternatively from 20 to 22 alkyl group. Mono-long alkyl amines can include mono-long alkyl amidoamines Primary, secondary, and tertiary fatty amines can be used.

Tertiary amido amines having an alkyl group of from about 19 to about 22 carbons. Exemplary tertiary amido amines include: behenamidopropyldimethylamine, behenamidopropyldiethylamine, behenamidoethyldiethylamine, behenamidoethyldimethylamine, brassicamidopropyldimethylamine, brassicamidopropyldiethylamine, brassicamidoethyldiethylamine, brassicamidoethyldimethylamine. Amines in the present invention are disclosed in U.S. Pat. No. 4,275,055, Nachtigal, et al.

In some examples, the conditioner composition can be substantially free of or free of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, arachidamidopropyldimethylamine, arachidamidopropyldiethyl amine, arachidamidoethyldiethylamine, arachidamidoethyldimethylamine, and/or diethylaminoethylstearamide.

These amines are used in combination with acids such as □-glutamic acid, lactic acid, hydrochloric acid, malic acid, succinic acid, acetic acid, fumaric acid, tartaric acid, citric acid, □-glutamic hydrochloride, maleic acid, and mixtures thereof; alternatively lactic acid, citric acid, at a molar ratio of the amine to the acid of from about 1:0.3 to about 1:2, alternatively from about 1:0.4 to about 1:1. The conditioner composition can contain from about 0.25 wt % to about 6 wt % acid, alternatively from about 0.4 wt % to about 5 wt % acid, from about 0.5 wt % to about 4 wt % acid, and alternatively from about 0.6 wt % to about 3 wt % acid.

In some examples, the conditioner composition can be free of mono long alkyl quaternized ammonium salts.

Di-Long Alkyl Quaternized Ammonium Salts

When used, di-long alkyl quaternized ammonium salts are alternatively combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts can have two long alkyl chains of from 12 to 30 carbon atoms, alternatively from 16 to 24 carbon atoms, alternatively from 18 to 22 carbon atoms.

Such di-long alkyl quaternized ammonium salts can have the formula (I):

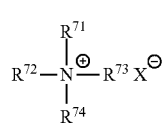

(I)

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Alternatively, two of $R^{71}$, $R^{72}$, $R^{73}$ and $R^{74}$ are selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Di-long alkyl cationic surfactants can include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 0.5 wt %, alternatively from about 0.8 wt %, alternatively from about 1.0 wt %, alternatively from about 1.2 wt %, even alternatively from about 1.5 wt %, and to about 30 wt %, alternatively to about 25 wt %, alternatively to about 20 wt %, alternatively to about 15 wt %, alternatively to about 12 wt % by weight of the composition, in view of providing the benefits of the present invention.

The high melting point fatty compound can have a melting point of 25° C. or higher, alternatively 40° C. or higher, alternatively 45° C. or higher, alternatively 47° C. or higher, alternatively 49° C. or higher, in view of stability of the emulsion especially the gel network. Alternatively, such melting point is up to about 90° C., alternatively up to about 80° C., alternatively up to about 75° C., even alternatively up to about 71° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound can be selected from the group consisting of fatty alcohols, fatty acids, and mixtures thereof. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are alternatively used in the composition of the present invention. The fatty alcohols can have from about 14 to about 30 carbon atoms, alternatively from about 16 to about 22 carbon atoms. These fatty alcohols are saturated and can be straight or branched chain alcohols.

Fatty alcohols can include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl, brassica or behenyl group.

The fatty alcohol may be selected from the group consisting of lauryl alcohol (C12), tridecyl alcohol (C13), myristyl alcohol (C14), pentadecyl alcohol (C15), cetyl alcohol (C16), isocetyl alcohol (C16), palmitoleyl alcohol (C16), heptadecyl alcohol (C17), stearyl alcohol (C18), isostearyl alcohol (C18), oleyl alcohol (C18), nonadecyl alcohol (C19), arachidyl alcohol (C20), heneicosyl alcohol (C21), behenyl alcohol (C22) erucyl alcohol (C22), lignoceryl alcohol (C24), ceryl alcohol (C26), brassica alcohol (C18-C22), cetostearyl alcohol (C16-C18), cetearyl alcohol (C16-C18), cetylstearyl alcohol (C16-C18) and combinations thereof.

The first fatty alcohol may have an alkyl chain average of C12 to C16 and the second fatty alcohol may have an alkyl chain average at least C18. The first fatty alcohol may have an alkyl chain average of C16 or lower. The second fatty alcohol may have an alkyl chain average from C18 to C26.

The molar ratio of the first fatty alcohol to the second fatty alcohol may be from about 25:75 to about 90:5, alternatively from about 25:75 to about 90:10, alternatively from about 30:70 to about 90:10, alternatively from about 35:65 to about 90:10. Such ratios are to ensure that all of the fatty alcohols are well incorporated into the gel network with BVE and form a creamy and uniform looking conditioner.

The fatty alcohol can be a mixture of cetyl alcohol (C16) stearyl alcohol (C18), behenyl alcohol (C22) and brassica alcohol (C18-C22). The first fatty alcohol may be cetyl alcohol, and the second alcohol may be stearyl alcohol (C18), behenyl alcohol (C22), and brassica alcohol (C18-C22).

Aqueous Carrier

The composition of the present invention can include an aqueous carrier. The level and species of the carrier can be selected according to the compatibility with other components, and other desired characteristic of the product.

The carrier can include water and water solutions of lower alkyl alcohols. The lower alkyl alcohols can be monohydric alcohols having 1 to 6 carbons, alternatively ethanol and isopropanol.

Alternatively, the aqueous carrier is substantially water. Deionized water is alternatively used. Water from natural sources including mineral cations can also be used, depending on the desired characteristic of the product. Generally, the compositions of the present invention comprise from about 40% to about 99%, alternatively from about 50% to about 95%, and alternatively from about 70% to about 93%, and alternatively from about 70% to about 92% water.

Gel Network

The gel network composition can be included in conditioner compositions to provide conditioning benefits, including improved wet feel of the hair after rinsing the conditioner. As used herein, the term "gel network" refers to a lamellar or vesicular solid crystalline phase which comprises at least one high melting point fatty compound, such as a fatty alcohol, as specified below, at least one surfactant, in particular a cationic surfactant, as specified below, and water or other suitable solvents. The lamellar or vesicular phase comprises bi-layers made up of a first layer comprising the high melting point fatty compound and the surfactant and alternating with a second layer comprising the water or other suitable solvent. Gel networks, generally, are further described by G. M. Eccleston, "Functions of Mixed Emulsifiers and Emulsifying Waxes in Dermatological Lotions and Creams", Colloids and Surfaces A: Physiochem. and Eng. Aspects 123-124 (1997) 169-182; and by G. M Eccleston, "The Microstructure of Semisolid Creams", Pharmacy International, Vol. 7, 63-70 (1986).

A gel network can be formed by the cationic surfactant, the high melting point fatty compound, and an aqueous carrier. The gel network is suitable for providing various conditioning benefits, such as slippery feel during the application to wet hair and softness and moisturized feel on dry hair.

Alternatively, when the gel network is formed, the cationic surfactant and the high melting point fatty compound are contained at a level such that the weight ratio of the cationic surfactant to the high melting point fatty compound is in the range of, from about 5:1 to about 1:20, alternatively from about 3:1 to about 1:15, alternatively from about 2:1 to about 1:12, alternatively from about 1:1 to about 1:10, alternatively from about 1:1 to about 1:9, in view of providing improved wet conditioning benefits.

To accurately predict cationic surfactants and fatty alcohols packing and forming gel network, molecular level of calculation is performed. The molar number of a cationic surfactant in the composition is calculated by the weight % of the cationic surfactant divided by its molecular weight. The molar number of a fatty alcohol in the composition is calculated similarly, which is the weight % of the fatty alcohol divided by the molecular weight of the fatty alcohol.

The total molar number of gel network content is the sum of molar number of cationic surfactants and fatty alcohols in the composition.

The molar ratio of cationic surfactants to fatty alcohols is the ratio of the total molar number of the cationic surfactants in the composition to the total molar number of the fatty alcohols in the composition.

Alternatively, when the gel network is formed, the cationic surfactant and the high melting point fatty compound are contained at a level such that the molar ratio of the cationic surfactant to the high melting point fatty compound is in the range of, from about 5:1 to about 1:20, alternatively from about 3:1 to about 1:15, alternatively from about 2:1 to about 1:12, alternatively from about 1.5:1 to about 1:10, alternatively from about 1.2:1 to about 1:9, alternatively from about 1:1 to about 1:9, in view of providing improved wet conditioning benefits.

Alternatively, especially when the gel network is formed, the composition of the present invention is substantially free of anionic surfactants, in view of stability of the gel network. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, alternatively 1% or less, alternatively 0.5% or less, alternatively 0.1% or less by weight of the composition. Most alternatively, the total level of such anionic surfactants is 0% by weight of the composition.

Silicone Compound

The compositions of the present invention may further contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 0.01 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1 to about 2,000,000 mPa-s, more preferably from about 100 to about 2,000,000 mPa-s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred.

The above polyalkylsiloxanes are available, for example, as a mixture with silicone compounds having a lower viscosity. Such mixtures have a viscosity of preferably from about 1,000 mPa-s to about 100,000 mPa-s, more preferably from about 5,000 mPa-s to about 50,000 mPa-s. Such mixtures preferably comprise: (i) a first silicone having a viscosity of from about 100,000 mPa-s to about 30,000,000 mPa-s at 25° C., preferably from about 100,000 mPa-s to about 20,000,000 mPa-s; and (ii) a second silicone having a viscosity of from about 5 mPa-s to about 10,000 mPa-s at 25° C., preferably from about 5 mPa-s to about 5,000 mPa-s. Such mixtures useful herein include, for example, a blend of dimethicone having a viscosity of 18,000,000 mPa-s and dimethicone having a viscosity of 200 mPa-s available from GE Toshiba, and a blend of dimethicone having a viscosity of 18,000,000 mPa-s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):
$(R_1)_a G_3\text{-a-Si}—(—OSiG_2)_n—(—OSiG_b(R_1)_{2\text{-}b})_m—O—SiG_3\text{-a(i)a}$ wherein G is hydrogen, phenyl, hydroxy, or Ci-C$_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; Ri is a monovalent radical conforming to the general formula $C_qH_{2q}L$, wherein q is an integer having a value from 2 to 8 and L is selected from the following groups: —N(R$_2$)CH$_2$—CH$_2$—N(R$_2$)2; —N(R$_2$)$_2$; —N(R$_2$)$_3$A⁻; —N(R$_2$)CH$_2$—CH$_2$—NR$_2$H$_2$A"; wherein R$_2$ is hydrogen, phenyl, benzyl, or a saturated hydrocarbon radical, preferably an alkyl radical from about Ci to about C$_2$O; A is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group. The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa-s to about 100,000 mPa-s, more preferably from about 5,000 mPa-s to about 50,000 mPa-s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof. Commercially available silicone emulsions useful herein include, for example, Belsil ADM 8301E, Belsil ADM 6300E available from Wacker, Silsoft 253 available from Momentive Silicone Polymer Containing Quaternary Groups Silicone compounds useful herein include, for example, a Silicone Polymer Containing Quaternary Groups comprising terminal ester groups, having a viscosity up to 100,000 mPa-s and a D block length of greater than 200 D units. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units. The silicone polymer is present in an amount of from about 0.05% to about 15%, preferably from about 0.1% to about 10%, more preferably from about 0.15% to about 5%, and even more preferably from about 0.2% to about 4% by weight of the composition.

In a preferred embodiment, the polyorganosiloxane compounds have the general formulas (Ia) and (Ib):

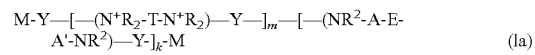

(Ia)

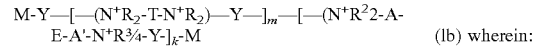

(Ib) wherein:

m is >0, preferred 0.01 to 100, more preferred 0.1 to 100, even more preferred 1 to 100, specifically 1 to 50, more specifically 1 to 20, even more specifically 1 to 10, k is 0 or an average value of from >0 to 50, or preferably from 1 to 20, or even more preferably from 1 to 10, M represents a terminal group, comprising terminal ester groups selected from

—OC(O)—Z

—OS(O)₂—Z

—OS(O₂)O—Z

—OP(O)(O—Z)OH

—OP(O)(O—Z)₂ wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

—[CH₂CH₂O]_q—[CH₂CH(CH₃)O]_r—[CH₂CH(C₂H₅)O]— wherein q=0 to 200, r=0 to 200, s=0 to 200, and q+r+s=1 to 600.

$R^2$ is selected from hydrogen or R,

R is selected from monovalent organic groups having up to 22 carbon atoms and optionally one or more heteroatoms, and wherein the free valencies at the nitrogen atoms are bound to carbon atoms, Y is a group of the formula:

—K—S—K— and -A-E-A'- or -A'-E-A-, wherein R1=Ci-C22-alkyl, Ci-C22-fluoroalkyl or aryl; n=200 to 1000, and these can be identical or different if several S Groups are present in the polyorganosiloxane compound. K is a bivalent or trivalent straight chain, cyclic and/or branched C2-C40 hydrocarbon residue which is optionally interrupted by —O—, —NH—, trivalent N, —$NR^1$—, —C(O)—, —C(S)—, and optionally substituted with —OH, wherein $R^1$ is defined as above, T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—($NR^2$-A-E-A'-$NR^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise:

A) at least one polyorganosiloxane compound, comprising a) at least one polyorganosiloxane group, b) at least one quaternary ammonium group, c) at least one terminal ester group, and d) at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides. In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa»s (100 Pa»s). In further embodiments, the viscosities of the neat silicone polymers may range from 500 to 100,000 mPa»s, or preferably from 500 to 70,000 mPa»s, or more preferably from 500 to 50,000 mPa»s, or even more preferably from 500 to 20,000 mPa»s. In further embodiments, the viscosities of the neat polymers may range from 500 to 10,000 mPa»s, or preferably 500 to 5000 mPa»s determined at 20° C. and a shear rate of 0.1 s$^{-1}$.

In addition to the above listed silicone polymers, the following preferred compositions are provided below. For example, in the polyalkylene oxide group E of the general formula:

—[CH₂CH₂O]_q—[CH₂CH(CH₃)O]_r—[CH₂CH(C₂H₅)O]— wherein the q, r, and s indices may be defined as follows:
q=0 to 200, or preferably from 0 to 100, or more preferably from 0 to 50, or even more preferably from 0 to 20,
r=0 to 200, or preferably from 0 to 100, or more preferably from 0 to 50, or even more preferably from 0 to 20,
s=0 to 200, or preferably from 0 to 100, or more preferably from 0 to 50, or even more preferably from 0 to 20,
and q+r+s=1 to 600, or preferably from 1 to 100, or more preferably from 1 to 50, or even more preferably from 1 to 40.

For polyorganosiloxane structural units with the general formula S:
$R^1$=Ci-C$_{22}$-alkyl, Ci-C$_{22}$-fluoralkyl or aryl; n=from 200 to 1000, or preferably from 300 to 500, K (in the group-K—S—K—) is preferably a bivalent or trivalent straight chain, cyclical or branched C2-C$_{20}$ hydrocarbon residue which is optionally interrupted by —O—, —NH—, trivalent N, —$NR^1$—, —C(O)—, —C(S)—, and optionally substituted with —OH.

In specific embodiments, $R^1$ is Ci-Ci$_8$ alkyl, Ci-Ci$_8$ fluoroalkyl and aryl. Furthermore, $R^1$ is preferably Ci-Ci$_8$ alkyl, Ci-C$_6$ fluoroalkyl and aryl. Furthermore, $R^1$ is more preferably Ci-C$_6$ alkyl, Ci-C$_6$ fluoroalkyl, even more preferably C1-C4 fluoroalkyl, and phenyl. Most preferably, $R^1$ is methyl, ethyl, trifluoropropyl and phenyl.

As used herein, the term "C1-C22 alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "C1-C22 fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples. Moreover, the term "aryl" means unsubstituted or phenyl substituted once or several times with OH, F, Cl, $CF_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

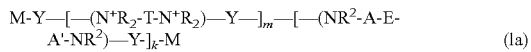

M-Y—[—($N^+R_2$-T-$N^+R_2$)—Y—]$_m$—[—($NR^2$-A-E-A'-$NR^2$)—Y-]$_k$-M (Ia)

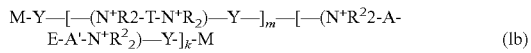

M-Y—[—($N^+R_2$-T-$N^+R_2$)—Y—]$_m$—[—($N^+R^2{}_2$-A-E-A'-$N^+R^2{}_2$)—Y-]$_k$-M (Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

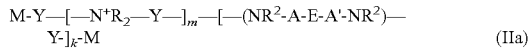

M-Y—[—$N^+R_2$—Y—]$_m$—[—($NR^2$-A-E-A'-$NR^2$)—Y-]$_k$-M (IIa)

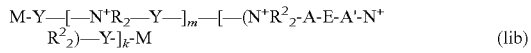

M-Y—[—$N^+R_2$—Y—]$_m$—[—($N^+R^2{}_2$-A-E-A'-$N^+R^2{}_2$)—Y-]$_k$-M (IIb)

wherein each group is as defined above. Also in such formula the repeating units are usually in a statistical arrangement (i.e not a block-wise arrangement). wherein, as defined above, M is

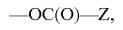
—OC(O)—Z,

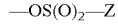
—OS(O)$_2$—Z

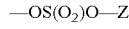
—OS(O$_2$)O—Z

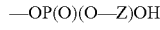
—OP(O)(O—Z)OH

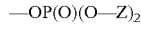
—OP(O)(O—Z)$_2$

Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or preferably between 20:1 and 1:20, or more preferably between 10:1 and 1:10.

In the group —($N^+R_2$-T-$N^+R_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, alternatively up to about 5% by weight of the composition.

A wide variety of other additional components can be formulated into the present compositions. These include:

a) Other conditioning agents such as aloe vera gel; aloe barbadensis leaf juice; ecklonia radiata extract; natural oils and waxes such as: shea butter, safflower oil, cocoa butter, orange peel wax, olive oil, macadamia seed oil, *Oenothera biennis* oil, *Crambe abyssinica* see oil, argon oil, camelina oil, sunflower oil, almond oil, argania spinosa kernel oil, grape see oil, jojoba oil, coconut oil, meadowfoam seed oil, neem oil, linseed oil, castor oil, soybean oil, sesame oil, beeswax, sunflower wax, candelilla wax, rice bran wax, carnauba wax, bayberry wax and soy wax; essential oils such as lime peel oil, lavender oil, peppermint oil, cedarwood oil, tea tree oil, ylang-ylang oil and coensage oil which can be used in fragrance; hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate; antioxidants include: rosemary, tocopherol, vitamin E, vitamin A and tea extracts; amino acids include histidine, 1-arginine and others.

b) Anti-Dandruff Actives,

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

c) Humectants

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

d) Water Miscible Solvents

The hair care composition described herein can comprise from about 0.1% to about 15%, alternatively from about 0.2% to about 10%, and alternatively from about 0.3% to about 5% of a water miscible solvent, by weight of the hair care composition. Alternatively, the hair care composition described herein can comprise from about 0.5% to about 10%, alternatively from about 0.75% to about 7.5%, alternatively from about 1% to about 5%, and alternatively from about 1.25% to about 3% of a water miscible solvent, by weight of the hair care composition.

The pressurized hair care composition described herein can comprise from about 0.1% to about 14%, alternatively from about 0.2% to about 9%, and alternatively from about 0.3% to about 5% of a water miscible solvent, by weight of the pressurized hair care composition. Alternatively, the pressurized hair care composition described herein can comprise from about 0.5% to about 9%, alternatively from about 0.75% to about 7%, alternatively from about 1% to about 5%, and alternatively from about 1.25% to about 3% of a water miscible solvent, by weight of the pressurized hair care composition.

Non-limiting examples of suitable water miscible solvents include polyols, copolyols, polycarboxylic acids, polyesters and alcohols.

Additional examples of useful polyols include, but are not limited to, glycerin, diglycerin, propylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Other suitable water miscible solvents include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

The water miscible solvents may be selected from the group consisting of glycerin, propylene glycol, dipropylene glycol, and mixtures thereof. EP 0283165 B1 discloses other suitable water miscible solvents, including glycerol derivatives such as propoxylated glycerol. The water miscible solvent may be selected from glycerin.

Product Forms

The compositions of the present invention can be in the form of rinse-off products or leave-on products and can be formulated in a wide variety of product forms, including but not limited to creams, gels, emulsions, mousses, and sprays.

The conditioning composition of the present invention is especially suitable for rinse-off hair conditioner. Such compositions are alternatively used by following steps:

(i) after shampooing hair, applying to the hair an effective amount of the conditioning compositions for conditioning the hair; and (ii) then rinsing the hair.

Test Methods

Bacterial Microbial Susceptibility Testing Method

Bacterial microbial susceptibility testing is used to assess the anti-bacterial effectiveness of the preservation system in cosmetic rinse-off conditioner.

A bacterial pool (mixture in equal volumes) of challenge organisms used in the test is comprised of standardized solutions of the bacterial strains *Escherichia coli* (ATCC #8739), *Staphylococcus aureus* (ATCC #6538), *Pseudomonas aeruginosa* (ATCC #9027), *Burkholderia cepacia* (ATCC #25416), as well as *Klebsiella pneumoniae, Enterobacter gergoviae* and *Serratia marcescens* strains isolated from cosmetic products. The bacterial pool is prepared to have a concentration of approximately 6-8 log cfu/ml. To start the test, 0.1 ml of the bacterial pool is added into 10.0 g of a test conditioner. The test conditioner is then incubated for 2 days at 20-25° C. After incubation, a 1.0 g aliquot of product is neutralized using Modified Letheen Broth containing 1.5% polysorbate 80 (commercially available as Tween® 80 from Croda™) and 1% Lecithin to aid in microbial recovery/enumeration. Then, multiple diluted concentrations of this sample are transferred into petri dishes containing Modified Letheen Agar with 1.5% Tween® 80, and the agar plates are incubated at least 2 days at 30-35° C. Bacterial colony forming units (cfus) are then enumerated, and a bacterial log reduction from the starting log cfu/g challenge level is reported.

A 1 log cfu/g reduction equates to ~a 90% bacterial reduction. A 2 log cfu/g reduction equates to ~a 99% bacterial reduction. A 3 log cfu/g reduction equates to ~a 99.9% bacterial reduction. A 4 log cfu/g reduction equates to ~a 99.99% bacterial reduction. Greater log cfu/g reduction values indicate greater antimicrobial robustness from the preservation system.

Fungal Microbial Susceptibility Testing Method:

Fungal microbial susceptibility testing is used to assess the anti-fungal effectiveness of the preservation system in cosmetic rinse-off conditioner.

Standardized ATCC strains of the yeast *Candida albicans* (ATCC #10231) and mold *Aspergillus brasiliensis* (frm. niger) (ATCC #16404) are mixed in 1:1 (v:v) ratio, and this fungal pool is used as inoculum in the test. The concentration of the fungal pool is approximately 6-8 log cfu/ml. To start the test, 0.1 ml of the fungal pool is added into 10.0 g of a testing conditioner. After the inoculated sample is incubated for 2 days at 20-25° C., a 1.0 g aliquot of product is neutralized using Modified Letheen Broth containing 1.5% Tween® 80 and 1% Lecithin to aid in microbial recovery/enumeration. Then, multiple diluted concentrations of this sample are transferred into petri dishes containing Modified Letheen Agar with 1.5% Tween 80, and the agar plates are incubated for at least 5 days at 20-25° C., at which time fungal colony forming units (cfus) are then enumerated, and a fungal log reduction from the starting log cfu/g challenge level is calculated.

A 1 log cfu/g reduction equates to ~a 90% fungal reduction. A 2 log cfu/g reduction equates to ~a 99% fungal reduction. A 3 log cfu/g reduction equates to ~a 99.9% fungal reduction. A 4 log cfu/g reduction equates to ~a 99.99% fungal reduction. Greater log cfu/g reduction values indicate greater anti-fungal robustness from the preservation system.

Differential Scanning Calorimetry

The melt transition behavior and temperature for the gel network may be obtained using differential scanning calorimetry (DSC) according to the following method. Utilizing a TA Instruments Q2000 DSC, approximately 15 mg of the gel network pre-mix or the final conditioner composition containing the gel network is placed into a Tzero aluminum hermetic DSC pan. The sample, along with an empty reference pan is placed into the instrument. The samples are analyzed using the following conditions/temperature program: Nitrogen Purge at a rate of 50.0 mL/min; Equilibrate @ 20.00° C.; Modulate+/−1.00° C./min every 60 seconds; until an isothermal is reach for 5.00 min; Ramp the temperature at a rate of 2.00° C./min to 90.00° C. The resulting DSC data is analyzed using TA Instruments Universal Analysis Software.

The use of DSC to measure the melt transition behavior and temperature for gel networks is further described by T. de Vringer et al., Colloid and Polymer Science, vol. 265, 448-457 (1987); and H. M. Ribeiro et al., Intl. J. of Cosmetic Science, vol. 26, 47-59 (2004).

pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 4 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe.

Submerse the electrode into the testing sample and press the read button. Wait until the pH icon stops flashing and record the value.

Shear Stress

Shear stress is measured by shear rate sweep condition with a rheometer available from TA Instruments with a mode name of ARG2. Geometry has 40 mm diameter, 2° C. cone angle, and gap of 49 μm. Shear rate is logarithmically increased from 0 to 1200/s for 1 min, and temperature is kept at 26.7° C. Share stress at a high shear rate of 950/s is measured and defined above.

Cone/Plate Viscosity Measurement

The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The liquid viscosity is determined using a steady state flow experiment at constant shear rate of $2\ s^{-1}$ and at temperature of 26.5° C. The sample size is 2.5 ml and the total measurement reading time is 3 minutes.

X-ray Diffraction Method

SAXS (Small Angle X-ray Scattering) is used to confirm the presence of a multi-lamellar phase, and WAXS (Wide Angle X-ray Scattering) is used to differentiate between L☐ (liquid) and Lβ (solid) crystalline structures were employed to verify the presence of the characteristic dispersed gel network phase of the personal conditioning compositions d-Spacing (Lβ-Basal Spacing) of Lamella Gel Network:

Small-angle x-ray scattering ("SAXS") as used to resolve periodic structures in mesophases is essentially an x-ray diffraction technique. It is used in conjunction with conventional wide-angle x-ray scattering ("WAXS") to characterize aggregate structures such as micelles, gel networks, lamella, hexagonal and cubic liquid crystals. The different mesophases that show periodic structures can be characterized by the relative positions (d-spacing) of their reflections as derived from the Bragg equation (d=λ/2 Sin θ) where d represents the interplanar spacing, λ the radiation wavelength and θ the scattering (diffraction) angle.

The one dimensional lamella gel network phase is characterized by the ratio of the interplanar spacings $d_1/d_1$, $d_1/d_2$, $d_1/d_3$, $d_1/d_4$, $d_1/d_5$ having the values 1:2:3:4:5 etc. in the SAXS region (long-range order) and one or two invariant reflection(s) in the WAXS region (short-range) centered around 3.5 and 4.5 Å over a broad halo background. Other mesophases (e.g. hexagonal or cubic) will have characteristically different d-spacing ratios.

The SAXS data was collected with a Bruker NanoSTAR small-angle x-ray scattering instrument. The micro-focus Cu x-ray tube was operated at 50 kV, 0.60 mA with 550 um ScanTex Pinholes. The sample to detector distance was 107.39 cm and the detector a Vantec2K 2-dimensional area detector. Samples were sealed in capillaries and analyzed under vacuum with an analysis time of 600 s.

The value of d-spacing ((Lβ-basal spacing) of lamella gel network reported here is obtained with the $1^{st}$ order of SAXS reflection which is the $d_1$ spacing.

WAXS confirmation (in combination with SAXS) of presence of LP Gel Network Wide-angle data (WAXS) was collected on a Stoe STADI-MP diffractometer. The generator was operated at 40 kV/40 mA, powering a copper anode long-fine-focus Cu x-ray tube. The diffractometer incorporates an incident-beam curved germanium-crystal monochromator, standard incident-beam slit system, and Mythen PSD detector. Data were collected in transmission mode over a range of 0° to 50° 2θ with a step size of 3° 2θ and 15 seconds per step.

WAXS Pattern with reflection near 4.2 Å which, in combination with the lamellar reflections seen in the SAXS, is indicative of the presence of Lβ gel network.

Hair Tress Evaluation Method:

Using a 1 mL syringe, apply 1 mL of leave-in-conditioner to 4 g 8" General Population hair tress. When applying product, start by placing the product midway through the hair tress and downwards towards the end of the tress. Once the 1 mL of product is has been placed on the hair tress, massage the product evenly throughout the hair tress. Once product is evenly applied and no white residue is visible, allow hair tress to air dry completely for over 24 hours. Then, the hair tresses were evaluated by a visual hair volume assessment and a dry combing assessment.

Visual Hair Volume Evaluation:

Once the hair tresses completely dried, conduct a visual check to evaluate the volume of hair tresses. Rate each hair tress on a scale of 1 to 10 on how much volume is perceived (10 is the most volume, 1 is the least volume).

Dry Combing Evaluation:

Once the hair tresses completely dried, use a fine-tooth comb to comb through each hair tress twice—once from the front of the tress and once from the back of the tress. Assess how much force is required for the comb to pass through the hair tress. Rate each hair tress on a scale of 1 to 10 on how much force is perceived to comb through (10 is the easiest, 1 is the hardest).

EXAMPLES

The following are non-limiting examples of the conditioner compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

The examples in Tables 2-11 were made as follows: BVE, fatty alcohols and oils/waxes were heated together as oil phase to 80° C. Sodium benzoate, glycerin, glyceryl esters and other water-soluble ingredients were heated together with water as water phase to 80° C. Pour hot water phase into hot oil phase and continue mixing well. Next, the mixture was cooled. Then, perfumes were added when the temperature was below 45° C. The composition was cooled to room temperature to make the conditioner composition.

Table 2 to Table 6 below, show Comparative Examples 1-23. Even though these compositions contain an effective surfactant system that is EWG VERIFIED™, do not contain any of the ingredients that Whole Foods® Market lists as unacceptable, are categorized as "risk-free" by the Yuka® Application, and can also meet the COSMOS-standard (Jan. 1, 2019), they are either not stable, or not consumer preferred.

TABLE 2

Comparative Examples 1-4

| | Camp. Ex. 1 | Camp. Ex. 2 | Camp. Ex. 3 | Camp. Ex. 4 |
|---|---|---|---|---|
| Appearance | Phase separation | Phase separation | Phase separation | Phase separation |
| AminoSensyl wt % (added) | 1.48 | 2.86 | 2.29 | 1.72 |
| AminoSensyl HC wt % (added) | 2.02 | 1.65 | 1.32 | 0.99 |
| Cetyl Alcohol (C16) wt % (active) | 1.42 | 1.14 | 0.91 | 0.68 |
| Glycerin wt % (active) | 5 | 5 | 5 | 5 |
| Glyceryl Caprylate and Glyceryl Undecylenate wt % (active) | 1.0 | 1.0 | 1.0 | 1.0 |
| Sodium Benzoate wt % (active) | 0.2 | 0.2 | 0.2 | 0.2 |
| Safflower oil wt % (active) | 0.84 | 0.84 | 0.84 | 0.84 |
| *Citrus Aurantium Dulcis* (orange) Wax wt % (active) | 0.16 | 0.16 | 0.16 | 0.16 |
| Perfume wt % (added) | 0.50 | 0.50 | 0.50 | 0.50 |
| Distilled Water | Q.S | Q.S | Q.S | Q.S |
| Adjust pH w Citric acid, L-Arginine or Calcium Gluconate to pH = 3 0-5.0 | | | | |
| Brassicyl Valinate Esylate wt % (active) | 1.90 | 3.11 | 2.48 | 1.86 |
| Brassica Alcohol (C18-C22) wt % (active) | 1.60 | 1.41 | 1.13 | 0.85 |
| Total GN content (Brassicyl Valinate Esylate + total FAOH molar) | 0.0147 | 0.0152 | 0.0122 | 0.0091 |
| Molar ratio of Brassicyl Valinate Esylate to total FAOH | 25 to 75 | 39 to 61 | 39 to 61 | 39 to 61 |
| Molar ratio of Cetyl Alcohol (C16) to Brassica Alcohol (C18-C22) | 53 to 47 | 51 to 49 | 51 to 49 | 51 to 49 |

In Comparative Examples 1-4, the gel network content is too low, meaning the compositions are not stable. The compositions exhibit phase separation, in which they become two phases after being placed in 50° C. room for one week. The inventive conditioner compositions have a gel network content from about 0.016 to about 0.06 molar.

TABLE 3a

Comparative Examples 5-7

| | Camp. Ex. 5 | Camp. Ex. 6 | Camp. Ex. 7 |
|---|---|---|---|
| Appearance | Grainy | Grainy | Grainy |
| AminoSensyl wt % (added) | 0.32 | 1.40 | |
| AminoSensyl HC wt % (added) | 6.10 | 5.68 | 12.20 |

TABLE 3a-continued

| Comparative Examples 5-7 | | | |
|---|---|---|---|
| | Camp. Ex. 5 | Camp. Ex. 6 | Camp. Ex. 7 |
| Cetyl Alcohol (C16) wt % (active) | 4.09 | 3.86 | 0.00 |
| Glycerin wt % (active) | 5 | 5 | 5 |
| Glyceryl Caprylate and Glyceryl Undecylenate wt % (active) | 1.0 | 1.0 | 1.0 |
| Sodium Benzoate wt % (active) | 0.2 | 0.2 | 0.2 |
| Safflower oil wt % (active) | 0.84 | 0.84 | 0.84 |
| *Citrus Aurantium Dulcis* (orange) Wax wt % (active) | 0.16 | 0.16 | 0.16 |
| Perfume wt % (added) | 0.50 | 0.50 | 0.50 |
| Distilled Water | Q.S | Q.S | Q.S |
| Adjust pH w Citric acid, L-Arginine or Calcium Gluconate to pH = 3.0-5.5 | | | |
| Brassicyl Valinate Esylate wt % (active) | 1.82 | 2.74 | 3.05 |
| Brassica Alcohol (C18-C22) wt % (active) | 4.60 | 4.34 | 9.15 |
| Total GN content (Brassicyl Valinate Esylate + total FAOH molar) | 0.0351 | 0.0352 | 0.0352 |
| Molar ratio of Brassicyl Valinate Esylate to total FAOH | 10 to 90 | 15 to 85 | 17 to 83 |
| Molar ratio of Cetyl Alcohol (C16) to Brassica Alcohol (C18-C22) | 53 to 47 | 53 to 47 | 0 to 100 |

In Comparative Examples 5-7, the molar ratio of BVE to fatty alcohol is too low and since there is too little BVE, not enough fatty alcohol was incorporated into the gel network. The examples appear to be grainy and non-uniform. The inventive conditioner composition can have a molar ratio of BVE to total fatty alcohol from about 20:80 to about 45:65.

TABLE 3b

| Comparative Examples 8-11 | | | | |
|---|---|---|---|---|
| | Camp. Ex. 8 | Camp. Ex. 9 | Camp. Ex. 10 | Camp. Ex. 11 |
| Appearance | Uniform | Uniform | Uniform | Uniform |
| Sheer stress (Pa) @ 950 1/s | 117 | 130 | 117 | 105 |
| Lβ gel network | not detected | not detected | not detected | not detected |
| AminoSensyl wt % (added) | 4.78 | 5.34 | 5.96 | 6.50 |
| AminoSensyl HC wt % (added) | 1.84 | 1.66 | 1.45 | 1.29 |
| Cetyl Alcohol (C16) wt % (active) | 1.23 | 1.11 | 0.98 | 0.86 |
| Glycerin wt % (active) | 5 | 5 | 5 | 5 |
| Glyceryl Caprylate and Glyceryl Undecylenate wt % (active) | 1.0 | 1.0 | 1.0 | 1.0 |
| Sodium Benzoate wt % (active) | 0.2 | 0.2 | 0.2 | 0.2 |
| Safflower oil wt % (active) | 0.84 | 0.84 | 0.84 | 0.84 |
| *Citrus Aurantium Dulcis* (orange) Wax wt % (active) | 0.16 | 0.16 | 0.16 | 0.16 |
| Perfume wt % (added) | 0.50 | 0.50 | 0.50 | 0.50 |
| Distilled Water | Q.S | Q.S | Q.S | Q.S |
| Adjust pH w Citric acid, L-Arginine or Calcium Gluconate to pH = 3.0-5.5 | | | | |
| Brassicyl Valinate Esylate wt % (active) | 4.95 | 5.44 | 5.96 | 6.43 |
| Brassica Alcohol (C18-C22) wt % (active) | 1.67 | 1.57 | 1.44 | 1.36 |
| Total GN content (Brassicyl Valinate Esylate + total FAOH molar) | 0.0200 | 0.0201 | 0.0202 | 0.0203 |
| Molar ratio of Brassicyl Valinate Esylate to total FAOH | 48 to 52 | 52 to 48 | 57 to 43 | 61 to 39 |
| Molar ratio of Cetyl Alcohol (C16) to Brassica Alcohol (C18-C22) | 49 to 51 | 48 to 52 | 47 to 53 | 45 to 55 |

In Comparative Examples 8-11, the molar ratio of BVE to fatty alcohol is too high, meaning there is too much BVE. No Lβ gel network was detected using x-ray scattering method. The examples do not provide consumer desired good wet conditioning feel. The inventive conditioner composition can have a molar ratio of BVE to total fatty alcohol from about 20:80 to about 45:65.

TABLE 4

| Comparative Examples 12-17 | | | | | | |
|---|---|---|---|---|---|---|
| | Camp. Ex. 12 | Camp. Ex. 13 | Camp. Ex. 14 | Camp. Ex. 15 | Camp. Ex. 16 | Camp. Ex. 17 |
| Appearance | Uniform | Uniform | Uniform | Uniform | Uniform | Uniform |
| Sheer stress (Pa) @ 950 1/s | 106 | 106 | 100 | 89 | 75 | 71 |
| Lβ gel network | additional microstructure possible | | | | | |
| AminoSensyl wt % (added) | 7.07 | 7.65 | 8.22 | 8.79 | 9.36 | 9.95 |
| AminoSensyl HC wt % (added) | 1.10 | 0.92 | 0.73 | 0.55 | 0.37 | 0.18 |
| Cetyl Alcohol (C16) wt % (active) | 0.74 | 0.62 | 0.49 | 0.37 | 0.25 | 0.12 |
| Glycerin wt % (active) | 5 | 5 | 5 | 5 | 5 | 5 |
| Glyceryl Caprylate and Glyceryl Undecylenate wt % (active) | 1.0 | 1.0 | 1.0 | 1.0 | 1.0 | 1.0 |
| Sodium Benzoate wt % (active) | 0.2 | 0.2 | 0.2 | 0.2 | 0.2 | 0.2 |
| Safflower oil wt % (active) | 0.84 | 0.84 | 0.84 | 0.84 | 0.84 | 0.84 |
| *Citrus Aurantium Dulcis* (orange) Wax wt % (active) | 0.16 | 0.16 | 0.16 | 0.16 | 0.16 | 0.16 |
| Perfume wt % (added) | 0.50 | 0.50 | 0.50 | 0.50 | 0.50 | 0.50 |
| Distilled Water | Q.S | Q.S | Q.S | Q.S | Q.S | Q.S |
| Adjust pH w Citric acid, L-Arginine or Calcium Gluconate to pH = 3.0-5.5 | | | | | | |
| Brassicyl Valinate Esylate wt % (active) | 6.93 | 7.42 | 7.91 | 8.40 | 8.89 | 9.40 |
| Brassica Alcohol (C18-C22) wt % (active) | 1.25 | 1.15 | 1.04 | 0.94 | 0.84 | 0.73 |
| Total GN content (Brassicyl Valinate Esylate + total FAOH molar) | 0.0204 | 0.0205 | 0.0206 | 0.0207 | 0.0208 | 0.0210 |
| Molar ratio of Brassicyl Valinate Esylate to total FAOH | 65 to 35 | 70 to 30 | 74 to 26 | 78 to 22 | 82 to 18 | 86 to 12 |
| Molar ratio of Cetyl Alcohol (C16) to Brassica Alcohol (C18-C22) | 43 to 57 | 41 to 59 | 38 to 62 | 34 to 66 | 27 to 73 | 18 to 82 |

In Comparative Examples 12-17, the molar ratio of BVE to fatty alcohol is too high and since there is an excess of BVE, additional microstructures were detected using x-ray scattering method, and no gel networks were formed. The examples do not provide consumer desired good wet conditioning feel. The inventive conditioner composition can have a molar ratio of BVE to total fatty alcohol from about 20:80 to about 45:65.

TABLE 5

| Comparative Examples 18-20 | | | |
|---|---|---|---|
| | Camp. Ex. 18 | Camp. Ex. 19 | Camp. Ex. 20 |
| Appearance | Grainy | Grainy | Grainy |
| AminoSensyl wt % (added) | 2.57 | 2.29 | 1.99 |
| AminoSensyl HC wt % (added) | 8.6 | 9.68 | 10.80 |
| Cetyl Alcohol (C16) wt % (active) | 1.27 | 0.65 | |
| Glycerin wt % (active) | 5 | 5 | 5 |
| Glyceryl Caprylate and Glyceryl Undecylenate wt % (active) | 1.0 | 1.0 | 1.0 |
| Sodium Benzoate wt % (active) | 0.2 | 0.2 | 0.2 |
| Safflower oil wt % (active) | 0.84 | 0.84 | 0.84 |
| *Citrus Aurantium Dulcis* (orange) Wax wt % (active) | 0.16 | 0.16 | 0.16 |
| Perfume wt % (added) | 0.5 | 0.50 | 0.50 |
| Distilled Water | Q.S | Q.S | Q.S |
| Adjust pH w Citric acid, L-Arginine or Calcium Gluconate to pH = 3.0-5.5 | | | |
| Brassicyl Valinate Esylate wt % (active) | 4.57 | 4.57 | 4.57 |
| Brassica Alcohol (C18-C22) wt % (active) | 6.6 | 7.40 | 8.22 |
| Total GN content (Brassicyl Valinate Esylate + total FAOH molar) | 0.0352 | 0.0352 | 0.0352 |
| Molar ratio of Brassicyl Valinate Esylate to total FAOH | 25 to 75 | 25 to 75 | 25 to 75 |
| Molar ratio of Cetyl Alcohol (C16) to Brassica Alcohol (C18-C22) | 20 to 80 | 10 to 90 | 0 to 100 |

In Comparative Examples 18, 19, and 20, the long chain fatty alcohol level is too high and the molar ratio of short chain fatty alcohol (cetyl alcohol C16) to long chain fatty alcohol (brassica alcohol C18-C22) is too low. The fatty alcohols could not be incorporated well into the gel network. The examples appear grainy and non-uniform. In contrast, the inventive conditioner composition can have a molar ratio of the shorter first fatty alcohol to the longer second fatty alcohol from about 25:75 to about 95:5, alternatively from about 25:75 to about 90:10, alternatively from about 30:70 to about 90:10, or alternatively from about 35:65 to about 90:10.

In Table 6 and Table 7 below, the Micro—Bacteria @ 2 days and the Micro—Fungi @ 2 days is determined by the Bacterial and Fungal Microbial Susceptibility Test Methods, described herein. For the preservative system to be effective, the level of microbes (bacteria and fungi) needs to be undetectable, which means that there is a greater than 99.99% reduction in microbes at two days as determined by the Bacterial and Fungal Microbial Susceptibility Test Methods.

TABLE 6

Comparative Examples 21 to 23.

|  | Camp. Ex. 21 | Camp. Ex. 22 | Camp. Ex. 23 |
|---|---|---|---|
| Appearance | Uniform | Uniform | Uniform |
| Sheer stress (Pa) @ 950 1/s |  | 109 | 161 |
| Lβ gel network d-spacing (nm) |  | 19.3 | 18.4 |
| Micro-Bacteria @ 2 day | ~90% reduction reduction | Not Detected using current method (>99.99%) | Not Detected using current method (>99.99%) |
| Micro-Fungui @ 2 days | ~90% reduction reduction | ~90% reduction reduction | ~90% reduction reduction |
| AminoSensyl wt % (added) | 3.62 | 3.62 | 4.47 |
| AminoSensyl HC wt % (added) | 4.80 | 4.80 | 6.00 |
| Cetyl Alcohol (C16) wt % (active) | 3.60 | 3.60 | 4.49 |
| Glycerin wt % (active) | 5 | 5 | 5 |
| Sodium Benzoate wt % (active) |  |  |  |
| Glyceryl Caprylate and Glyceryl Undecylenate wt % (active) |  | 1.0 | 1.0 |
| Safflower oil wt % (active) | 0.80 | 0.80 | 0.55 |
| *Citrus Aurantium Dulcis* (orange) Wax wt % (active) | 0.20 | 0.20 |  |
| *Theobroma Cacoa* (Cocoa) Seed Butter wt % (active) |  |  | 0.50 |
| Perfume wt % (added) | 0.50 | 0.50 | 0.33 |
| Distilled Water | Q.S | Q.S | Q.S |
| Adjust pH w Citric acid, L-Arginine or Calcium Gluconate to pH = 3.0-5.5 | | | |
| Brassicyl Valinate Esylate wt % (active) | 4.60 | 4.60 | 5.70 |
| Brassica Alcohol (C18-C22) wt % (active) | 3.82 | 3.82 | 4.77 |
| Total GN content (Brassicyl Valinate Esylate + total FAOH molar) | 0.0360 | 0.0360 | 0.0448 |
| Molar ratio of Brassicyl Valinate Esylate to total FAOH | 25 to 75 | 25 to 75 | 25 to 75 |
| Molar ratio of Cetyl Alcohol (C16) to Brassica Alcohol (C18-C22) | 55 to 45 | 55 to 45 | 55 to 45 |

Comparative examples 21 does not contain a preservative system at all, which does not provide enough microbe reduction at 2 days for bacteria and fungi.

Comparative examples 22 and 23 contain 1 wt % of glyceryl caprylate (and) glyceryl undeylenate (glyceryl esters), that is, they comprise only one preservative. These examples have an undetectable level (>99.99% reduction) of bacteria at two days. However, they do not provide enough fungi reduction at two days, as these examples only have a ~90% reduction.

TABLE 7

Examples 1-3

|  | Ex. 1 | Ex. 2 | Ex. 3 |
|---|---|---|---|
| Appearance | Uniform | Uniform | Uniform |
| Sheer stress (Pa) @ 950 1/s | 198 | 355 | 220 |
| Lβ gel network d-spacing (nm) | 19.8 | 17.9 | 18.2 |
| Micro-Bacteria @ 2 day | Not Detected using current method (>99.99%) | | |

TABLE 7-continued

Examples 1-3

|  | Ex. 1 | Ex. 2 | Ex. 3 |
|---|---|---|---|
| Micro-Fungui @ 2 days | Not Detected using current method (>99.99%) | | |
| AminoSensyl wt % (added) | 3.62 | 4.47 | 4.47 |
| AminoSensyl HC wt % (added) | 4.80 | 6.00 | 6.00 |
| Cetyl Alcohol (C16) wt % (active) | 3.60 | 4.49 | 4.49 |
| Glycerin wt % (active) | 5 | 5 | 5 |
| Sodium Benzoate wt % (active) | 0.2 | 0.2 | 0.2 |
| Glyceryl Caprylate and Glyceryl Undecylenate wt % (active) | 1.0 | 1.0 | |
| Glyceryl Caprylate wt % (active) | | | 1.0 |
| Safflower oil wt % (active) | 0.80 | 0.55 | 0.55 |
| *Citrus Aurantium Dulcis* (orange) Wax wt % (active) | 0.20 | | |
| *Theobroma Cacoa* (Cocoa) Seed Butter wt % (active) | | 0.50 | 0.50 |
| Perfume wt % (added) | 0.50 | 0.33 | 0.33 |
| Distilled Water | Q.S | Q.S | Q.S |
| Adjust pH w Citric acid, L-Arginine or Calcium Gluconate to pH = 3.0-5.5 | | | |
| Brassicyl Valinate Esylate wt % (active) | 4.60 | 5.70 | 5.70 |
| Brassica Alcohol (C18-C22) wt % (active) | 3.82 | 4.77 | 4.77 |
| Total GN content (Brassicyl Valinate Esylate + total FAOH molar) | 0.0360 | 0.0448 | 0.0448 |
| Molar ratio of Brassicyl Valinate Esylate to total FAOH | 25 to 75 | 25 to 75 | 25 to 75 |
| Molar ratio of Cetyl Alcohol (C16) to Brassica Alcohol (C18-C22) | 55 to 45 | 55 to 45 | 55 to 45 |

In Table 7, examples 1 and 2 contain 0.2 wt % sodium benzoate and 1.0 wt % of glyceryl caprylate (and) glyceryl undeylenate, while example 3 contains 0.2 wt % sodium benzoate and 1.0 wt % of glyceryl caprylate. All of the Examples in Table 7 have preservative systems that are effective (i.e. bacteria and fungi are not detectable (>99.99% reduction at 2 days) and uniform, a creamy and smooth appearance that is consumer preferred.

All of the examples in Table 8 and Table 11 below, examples 4 to 23 contain the same effective natural preservative system as examples 1 to 3, which comprising 0.2 wt % sodium benzoate and 1.0 wt % glyceryl esters. Examples 1 to 21 are inventive examples.

TABLE 8

Examples 4-9

|  | Ex. 4 | Ex. 5 | Ex. 6 | Ex. 7 | Ex. 8 | Ex. 9 |
|---|---|---|---|---|---|---|
| Appearance | Uniform | Uniform | Uniform | Uniform | Uniform | Uniform |
| Sheer stress (Pa) @ 950 1/s | 230 | 205 | 227 | 306 | 303 | 297 |
| Lβ gel network d-spacing (nm) | 20.0 | 20.0 | 19.5 | 19.0 | 19.0 | 17.9 |
| AminoSensyl wt % (added) | 2.48 | 3.57 | 4.65 | 5.74 | 6.82 | 7.90 |
| AminoSensyl HC wt % (added) | 5.25 | 4.82 | 4.40 | 3.97 | 3.54 | 3.12 |
| Cetyl Alcohol (C16) wt % (active) | 3.64 | 3.41 | 3.18 | 2.95 | 2.73 | 2.50 |
| Glycerin wt % (active) | 5 | 5 | 5 | 5 | 5 | 5 |
| Glyceryl Caprylate and Glyceryl Undecylenate wt % (active) | 1.0 | 1.0 | 1.0 | 1.0 | 1.0 | 1.0 |
| Sodium Benzoate wt % (active) | 0.2 | 0.2 | 0.2 | 0.2 | 0.2 | 0.2 |
| Safflower oil | 0.84 | 0.84 | 0.84 | 0.84 | 0.84 | 0.84 |
| *Citrus Aurantium Dulcis* (orange) Wax | 0.16 | 0.16 | 0.16 | 0.16 | 0.16 | 0.16 |
| Perfume | 0.50 | 0.50 | 0.50 | 0.50 | 0.50 | 0.50 |
| Distilled Water | Q.S | Q.S | Q.S | Q.S | Q.S | Q.S |
| Adjust pH w Citric acid, L-Arginine or Calcium Gluconate to pH = 3.0-5.5 | | | | | | |
| Brassicyl Valinate Esylate wt % (active) | 3.65 | 4.56 | 5.47 | 6.38 | 7.30 | 8.21 |
| Brassica Alcohol (C18-C22) wt % (active) | 4.09 | 3.83 | 3.58 | 3.32 | 3.06 | 2.81 |
| Total GN content (Brassicyl Valinate Esylate + total FAOH molar) | 0.0352 | 0.0351 | 0.0352 | 0.0351 | 0.0351 | 0.0352 |
| Molar ratio of Brassicyl Valinate Esylate to total FAOH | 25 to 75 | 25 to 75 | 30 to 70 | 35 to 65 | 40 to 60 | 45 to 55 |

TABLE 8-continued

Examples 4-9

|  | Ex. 4 | Ex. 5 | Ex. 6 | Ex. 7 | Ex. 8 | Ex. 9 |
|---|---|---|---|---|---|---|
| Molar ratio of Cetyl Alcohol (C16) to Brassica Alcohol (C18-C22) | 53 to 47 | 53 to 47 | 53 to 47 | 53 to 47 | 53 to 47 | 53 to 47 |

TABLE 9

Examples 10-15

|  | Ex. 10 | Ex. 11 | Ex. 12 | Ex. 13 | Ex. 14 | Ex. 15 |
|---|---|---|---|---|---|---|
| Appearence | Uniform | Uniform | Uniform | Uniform | Uniform | Uniform |
| Sheer stress (Pa) @ 950 1/s | 97 | 83 | 84 | 90 | 98 | 118 |
| Lβ gel network d-spacing (nm) | 24.9 | 24.6 | 24.8 | 24.2 | 23.9 | 23.2 |
| AminoSensyl wt % (added) | 1.33 | 1.93 | 2.54 | 3.04 | 3.72 | 4.19 |
| AminoSensyl HC wt % (added) | 2.94 | 2.62 | 2.53 | 2.40 | 2.15 | 2.03 |
| Cetyl Alcohol (C16) wt % (active) | 1.97 | 1.85 | 1.72 | 1.60 | 1.48 | 1.35 |
| Glycerin wt % (active) | 5 | 5 | 5 | 5 | 5 | 5 |
| Glyceryl Caprylate and Glyceryl Undecylenate wt % (active) | 1.0 | 1.0 | 1.0 | 1.0 | 1.0 | 1.0 |
| Sodium Benzoate wt % (active) | 0.2 | 0.2 | 0.2 | 0.2 | 0.2 | 0.2 |
| Safflower oil | 0.84 | 0.84 | 0.84 | 0.84 | 0.84 | 0.84 |
| *Citrus Aurantium Dulcis* (orange) Wax | 0.16 | 0.16 | 0.16 | 0.16 | 0.16 | 0.16 |
| Perfume | 0.50 | 0.50 | 0.50 | 0.50 | 0.50 | 0.50 |
| Distilled Water | Q.S | Q.S | Q.S | Q.S | Q.S | Q.S |
| Adjust pH w Citric acid, L-Arginine or Calcium Gluconate to pH = 3.0-5.5 | | | | | | |
| Brassicyl Valinate Esylate wt % (active) | 1.99 | 2.47 | 3.03 | 3.46 | 4.04 | 4.45 |
| Brassica Alcohol (C18-C22) wt % (active) | 2.29 | 2.08 | 2.05 | 1.98 | 1.83 | 1.77 |
| Total GN content (Brassicyl Valinate Esylate +total FAOH molar) | 0.0193 | 0.0191 | 0.0195 | 0.0196 | 0.0198 | 0.0198 |
| Molar ratio of Brassicyl Valinate Esylate to total FAOH | 20 to 80 | 25 to 75 | 30 to 70 | 34 to 66 | 39 to 61 | 43 to 57 |
| Molar ratio of Cetyl Alcohol (C16) to Brassica Alcohol (C18-C22) | 53 to 47 | 53 to 47 | 52 to 48 | 51 to 49 | 51 to 49 | 50 to 50 |

TABLE 10

Examples 16-19

|  | Ex. 16 | Ex. 17 | Ex. 18 | Ex. 19 |
|---|---|---|---|---|
| Appearance | Uniform | Uniform | Uniform | Uniform |
| Sheer stress (Pa) @ 950 1/s | 88 | 95 | 163 | 222 |
| Lβ gel network d-spacing (nm) | 24.2 | 23.5 | 21.2 | 19.3 |
| AminoSensyl wt % (added) | 1.89 | 2.38 | 2.97 | 3.62 |
| AminoSensyl HC wt % (added) | 2.77 | 3.21 | 4.02 | 4.8 |
| Cetyl Alcohol (C16) wt % (active) | 1.85 | 2.27 | 2.84 | 3.6 |
| Glycerin wt % (active) | 5 | 5 | 5 | 5 |
| Glyceryl Caprylate and Glyceryl Undecylenate wt % (active) | 1 | 1 | 1 | 1 |
| Sodium Benzoate wt % (active) | 0.2 | 0.2 | 0.2 | 0.2 |
| Safflower oil wt % (active) | 0.84 | 0.84 | 0.84 | 0.84 |
| *Citrus Aurantium Dulcis* (orange) Wax % (active) | 0.16 | 0.16 | 0.16 | 0.16 |
| Perfume wt % (added) | 0.5 | 0.5 | 0.5 | 0.5 |
| Distilled Water | Q.S | Q.S | Q.S | Q.S |
| Adjust pH w Citric acid, L-Arginine or Calcium Gluconate to pH = 3.0-5.0 | | | | |
| Brassicyl Valinate Esylate wt % (active) | 2.47 | 3.04 | 3.8 | 4.6 |
| Brassica Alcohol (C18-C22) wt % (active) | 2.19 | 2.55 | 3.19 | 3.82 |

TABLE 10-continued

Examples 16-19

|  | Ex. 16 | Ex. 17 | Ex. 18 | Ex. 19 |
|---|---|---|---|---|
| Total GN content (Brassicyl Valinate Esylate + total FAOH molar) | 0.0194 | 0.0234 | 0.0293 | 0.036 |
| Molar ratio of Brassicyl Valinate Esylate to total FAOH | 25 to 75 | 25 to 75 | 25 to 75 | 25 to 75 |
| Molar ratio of Cetyl Alcohol (C16) to Brassica Alcohol (C18-C22) | 52 to 48 | 53 to 47 | 53 to 47 | 55 to 45 |

TABLE 11

Examples 20-21

|  | Ex. 20 | Ex. 21 |
|---|---|---|
| Apparence | Uniform | Uniform |
| Sheer stress (Pa) @ 950 1/s | 188 | 224 |
| Lβ gel network d-spacing (nm) |  |  |
| AminoSensyl wt % (added) | 4.66 | 4.07 |
| AminoSensyl HC wt % (added) | 0.72 | 2.96 |
| Cetyl Alcohol (C16) wt % (active) | 5.74 | 4.47 |
| Glycerin wt % (active) | 5 | 5 |
| Glyceryl Caprylate and Glyceryl Undecylenate wt % (active) | 1 | 1 |
| Sodium Benzoate wt % (active) | 0.2 | 0.2 |
| Safflower oil wt % (active) | 0.84 | 0.84 |
| *Citrus Aurantium Dulcis* (orange) Wax wt % (active) | 0.16 | 0.16 |
| Perfume wt % (added) | 0.5 | 0.5 |
| Distilled Water | Q.S | Q.S |
| Adjust pH w Citric acid, L-Arginine or Calcium Gluconate to pH = 3.0-5.5 |  |  |
| Brassicyl Valinate Esylate wt % (active) | 4.56 | 4.57 |
| Brassica Alcohol (C18-C22) wt % (active) | 0.82 | 2.46 |
| Total GN content (Brassicyl Valinate Esylate + total FAOH molar) | 0.0351 | 0.0352 |
| Molar ratio of Brassicyl Valinate Esylate to total FAOH | 25 to 75 | 25 to 75 |
| Molar ratio of Cetyl Alcohol (C16) to Brassica Alcohol (C18-C22) | 90 to 10 | 70 to 30 |

Examples 1 to 21 are inventive examples. The shear stress of Examples 1 to 21 is consumer acceptable and ranges from 70 Pa to 800 Pa. If the shear stress is too low or too high it can be difficult for a consumer to apply the conditioner composition throughout their hair with their hands. If the shear stress is too low, the conditioner composition can drip from the hand and hair, and if the shear stress is too high, it can be difficult to spread.

The gel network d-spacing is from 15 nm to 40 nm for Examples 1-21. This level of d-spacing indicates that the conditioner composition can provide good conditioning with good wet feel and good wet detangling.

Examples 1-21 have a molar ratio of BVE to FAOH of greater than or equal to 20:80 and less than or equal to 45:55.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A hair conditioner composition consisting of:
a. water
b. from about 1 wt % to about 12 wt % of Brassicyl valinate esylate
c. from about 1 wt % to about 12 wt % of two fatty alcohols, wherein the first fatty alcohol is cetyl alcohol and the second fatty alcohol is selected from the group consisting of brassica alcohol, stearyl alcohol and behenyl alcohol
d. a preservative system consisting of i. from about 0.1 wt % to about 1.5 wt % of a first preservative, wherein the first preservative is sodium benzoate or potassium sorbate; and ii. from about 0.2 wt % to about 2.0 wt % of a second preservative, wherein the second preservative is selected from the group consisting of glyceryl caprylate, glyceryl caprate, glyceryl undecylenate and mixtures thereof,
   wherein the preservative system is free of a preservative ingredient selected from the group consisting of ethylenediaminetetraacetic acid, salts of ethylenediaminetetraacetic acid, isothiazolinones, benzyl alcohol, phenoxyethanol, cyclohexyl glycerin, parabens, and combinations thereof,
e. Amino sensyl
f. glycerin
g. Safflower oil
h. orange wax
i. perfume
j. citric acid, L-Argininc or Calcium gluconate
wherein the molar ratio of the first fatty alcohol to the second fatty alcohol is from about 25:75 to 90:10;
wherein the molar ratio of Brassicyl valinate esylate to total fatty alcohol is from about 20:80 to about 35:65;
wherein the composition comprises a uniform Lβgel network; wherein the composition comprises d-spacing of from about 15 nm to about 40 nm, wherein the composition has a shear stress from about 70 Pa to 800 Pa @ 950 l/s and wherein the composition is free of behentrimonium chloride, behentrimonium methosulfate, cetrimonium chloride, stearamidopropyl dimethylamine, brassicamidopropyl dimethylamine, behenamidopropyl dimethylamine, quaternized ammonium salts, amidoamines, silicone, propellants, phthalates, dyes, sulfates, formaldehyde donors, and combinations thereof.

2. The hair conditioner composition of claim 1, wherein the Lβ gel network content is from about 0.016 molar to about 0.06 molar.

3. The hair conditioner composition of claim 1, comprising a shear stress of from about 75 Pa to about 700 Pa.

4. The hair conditioner composition of claim 1, comprising a pH from about 2.5 to about 5.5.

5. The hair conditioner composition of claim 1, wherein sodium benzoate is from about 0.1% to about 0.8%, by weight of the composition.

6. The hair conditioner composition of claim 1, wherein the second preservative is from about 0.2% to about 1.5%, by weight of the composition.

7. The hair conditioner composition of claim 1, wherein the second preservative is from about 0.35% to about 0.5%, by weight of the composition.

* * * * *